United States Patent [19]

Langston et al.

[11] 4,241,733
[45] Dec. 30, 1980

[54] PATIENT-CARE APPARATUS WITH DEVICE FOR DISPENSING ANTI-PATHOGENIC AGENT

[75] Inventors: Jimmy B. Langston, San Jose; Harold Leeper, Mountain View; Patrick S. Wong, Palo Alto, all of Calif.

[73] Assignee: ALZA Corporation, Palo Alto, Calif.

[21] Appl. No.: 78,507

[22] Filed: Sep. 24, 1979

Related U.S. Application Data

[62] Division of Ser. No. 804,962, Jun. 9, 1977, Pat. No. 4,193,403.

[51] Int. Cl.³ .............................................. A61F 5/44
[52] U.S. Cl. ..................................... 128/275; 128/295
[58] Field of Search ............... 128/272, 275, 283, 294, 128/295, DIG. 24

[56] References Cited

U.S. PATENT DOCUMENTS

| | | | |
|---|---|---|---|
| 785,838 | 3/1905 | Sutor | 128/196 |
| 1,080,716 | 12/1913 | Rand, Jr. | 239/55 |
| 2,149,053 | 2/1939 | Hollister | 128/283 |
| 3,312,221 | 4/1967 | Overment | 128/275 |
| 3,694,146 | 9/1972 | Roy et al. | 21/119 |
| 3,832,999 | 9/1974 | Crilly | 128/275 |
| 3,848,603 | 11/1974 | Throner | 128/349 R |

*Primary Examiner*—C. Fred Rosenbaum
*Attorney, Agent, or Firm*—Paul L. Sabatine; Edward L. Mandell; Thomas E. Ciotti

[57] ABSTRACT

A patient-care apparatus housing a device for controlling the presence of pathogens is disclosed. The apparatus comprises a container with an inlet port and a device in the apparatus for controlling the presence of pathogens.

4 Claims, 3 Drawing Figures

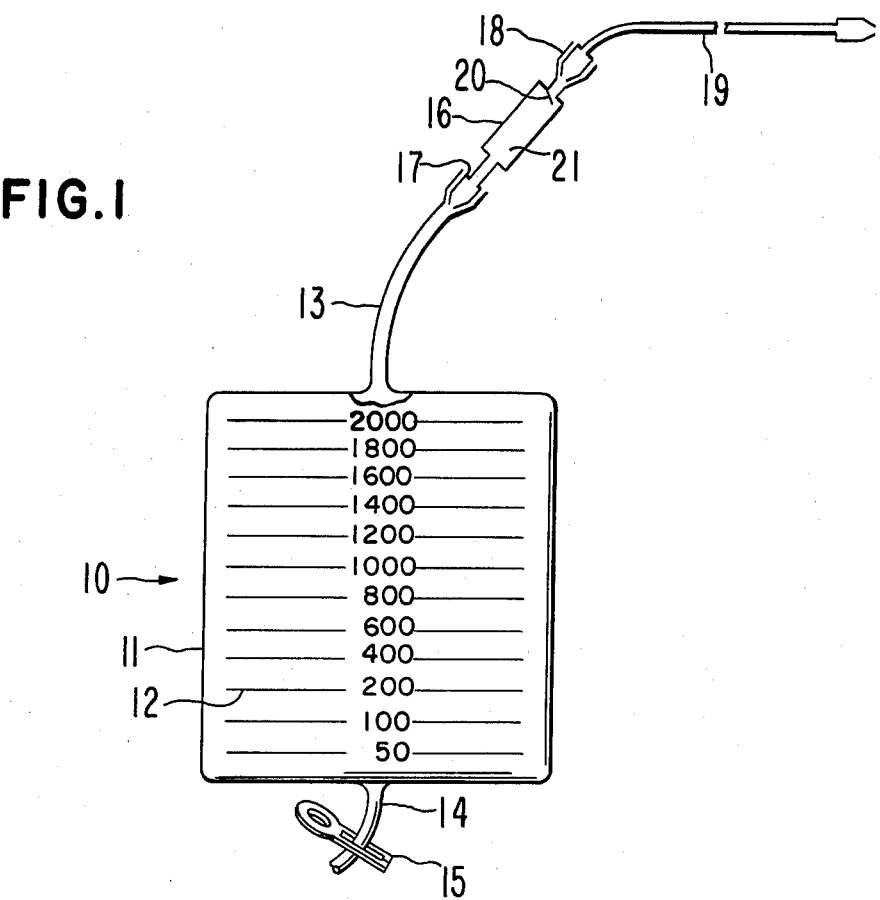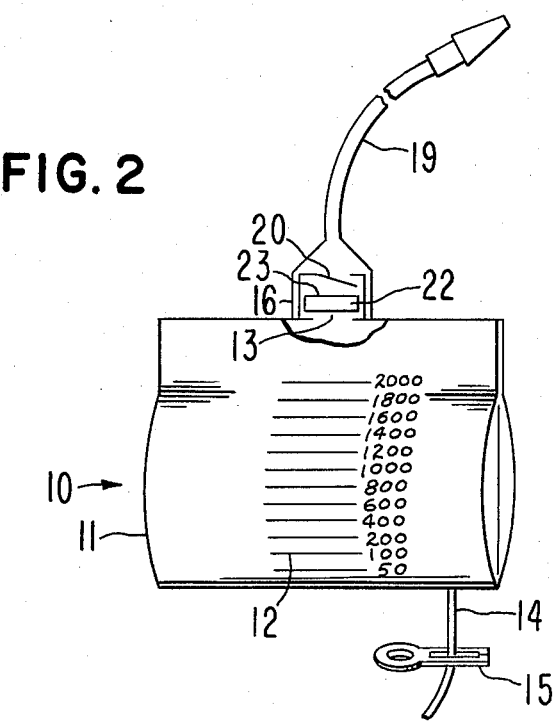

PATIENT-CARE APPARATUS WITH DEVICE FOR DISPENSING ANTI-PATHOGENIC AGENT

CROSS-REFERENCE TO RELATED APPLICATION

This application is a division of U.S. Pat. Application Ser. No. 804,962 filed on June 9, 1977, now U.S. Pat. No. 4,193,403, which is incorporated herein by reference and benefit is claimed of its filing date.

FIELD OF THE INVENTION

This invention pertains to patient-care apparatus. More specifically, the invention relates to patient-care apparatus comprising a container and a catheter having in combination with the apparatus a dispensing device that releases an agent for preventing and controlling the presence of unwanted pathogens in the entire apparatus and more particularly in the catheter. The invention also concerns a method for using the device in cooperation with the apparatus.

BACKGROUND OF THE INVENTION

It is now generally acknowledged that indwelling catheterization in medical, surgical, gynecological, urological and other patients leads to serious infection of the urogenital tract. Despite the use of most careful aseptic techniques undertaken while the catheter is in the patient, approximately fifty percent of the patients develop an infection when a catheter is in place for twenty four hours, and approximately ninety-eight to one hundred percent of the patients develop an infection after four days of open indwelling catheter drainage. This is harmful to the patient because they are subjected to the risk of cystitis, acute pyelonephritis, and life-threatening septicemia which carries a risk of mortality, as reported in *Arch. Internal Med.*, Vol. 110, pages 703 to 711, 1962; *Antimicrob. Agents Chemother.*, pages 617 to 623, 1963; and, *Lancet* Vol. 1, pages 310 to 312, 1960.

The occurrence of the above-mentioned infection is encouraged by many circumstances. These include prolonged use of indwelling Foley catheters often accompanied by the absence of sterile insertion and maintenance techniques, having the catheter connected to clean but not sterile drainage collection containers placed in the immediate vicinity of the patient's bed. The presence of urinary pathogens in the container which multiply and enter the tract through the ascending catheter which is a major pathway of infection, the use of drainage systems made without a valve designed to prevent ascending pathogen migration through the catheter, and the use of nonprofessional ward personnel for monitoring the indwelling catheter and the drainage system. These and other circumstances that predispose a patient to infection are reported in *Urinary Tract Infection and Its Management*, edited by Kaye, D., Chapter 15, *Care of the Indwelling Catheter*, pages 256 to 266, 1972, published by the C. V. Mosby Company, St. Louis, Mo.

Attempts have been made to reduce the incidence of catheter-acquired infection, but these have not met with general acceptance. For example, one such attempt consists of systemic chemoprophylaxis achieved by administering either chloramphenicol or penicillin and streptomycin but this affords no significant protection against the acquisition of infection after indwelling catheterization as reported in *Arch. Internal Med.*, Vol. 110, pages 703 to 711, 1962; *Acta Chiv. Scand.*, Vol. 118, pages 45 to 52, 1959; and *Dis. Mon.*, pages 1 to 36, September 1960. Another attempt for controlling infection consists in adding formalin to the collection container. However, this method does not enjoy general use because there is a risk of siphoning formalin into the urinary tract, and more importantly, since the formalin is in the container distant from the catheter, it does not provide any protection against pathogens traveling an ascending catheter; see *British Medical Journal*, Vol. 2, pages 423 to 425, 1964. One other attempt known to the art for preventing infection consists in placing an interruption in the catheter to prevent pathogen migration from a container to the patient. The purpose of the interruption was to discourage communication of the infection to the patient, as disclosed in U.S. Pat. No. 3,750,372. This design, however, is not widely used as it lacks means for preventing pathogen multiplication in the entire collection system and because the presence of small amounts of moisture in the interruption acts as a highway for pathogens can travel to the patient. In U.S. Pat. No. 3,908,659 one way valves are disclosed for establishing in drainage systems a barrier to pathogen migration; but these, too, are unsatisfactory because the valve retains liquid which liquid then provides the pathogens with a path around the barrier. It will be appreciated by those versed in the art, that in view of the above presentation, a critical need exists for a patient care collection system having in cooperation therewith a device for preventing and controlling the presence of unwanted pathogens in the system, and if such were made available, it would represent a valuable and useful contribution to the practicing art.

OBJECTS OF THE INVENTION

Accordingly, it is an object of the present invention to provide an improvement in patient care apparatus which improvement overcomes the disadvantages associated with the prior art.

It is a further object of the invention to provide a patient care apparatus comprising in combination a drainage collection system and a dispensing device for preventing the multiplication of/and controlling the migration of pathogens from the system into a patient.

Still a further object of the invention is to provide a patient care apparatus consisting of a fluid collection container and a catheter with a housing for holding a dispensing device that releases an agent for preventing passage of unwanted pathogens through the catheter into a mammalian host.

Yet still a further object of the invention is to make available to the medico-surgical art a patient care urinary drainage collection system housing a dispensing device containing a polymer that is depolymerized in the presence of moisture and released from the device as an active agent that essentially discourages the communication of infection producing pathogenic organisms from the system back into the patient.

It is yet another object of this invention to provide a urinary drainage system with a detachable housing for containing a dispensing device that releases an antipathogenic agent and which system embraces inventive simplicity, is inexpensive to make and is disposable.

Another object of the invention is to provide a urinary container which container has a dispensing device that releases an agent for controlling the presence of pathogens.

These and other objects of the present invention will become more apparent upon a consideration of the drawings, the specification and the accompanying claims.

SUMMARY OF THE INVENTION

This invention concerns a patient care apparatus comprising, in combination, a container having an inlet port, an exit port and a housing adapted for communicating with the inlet port and adapted for receiving a catheter. The housing contains a dispensing device containing a polymer which in the device or on its release therefrom is depolymerized to formaldehyde. The latter compound is useful for controlling the multiplication of pathogens in the apparatus and for preventing their migration into a patient. An aspect of the invention concerns the presence of a dispensing device within the container for controlling the presence of pathogens.

BRIEF DESCRIPTION OF THE DRAWINGS

In the drawings, which are not drawn to scale, but rather are set forth to illustrate various embodiments of the invention, the figures are as follows:

FIG. 1 is a frontal view of a patient care apparatus of the invention showing a container acting in cooperation with a detachable housing for holding a dispensing device;

FIG. 2 is a partially frontal view of the patient care apparatus illustrating the housing for holding the dispensing device in communication with the container; and, FIG. 3 illustrates the patient care apparatus with the dispensing device in the container.

In the specification and drawings, like parts in related figures are identified by like numbers. The terms appearing earlier in the specification and in the description of the drawings, as well as embodiments thereof are further discussed elsewhere in the disclosure.

DETAILED DESCRIPTION OF THE DRAWINGS

Figure 3:
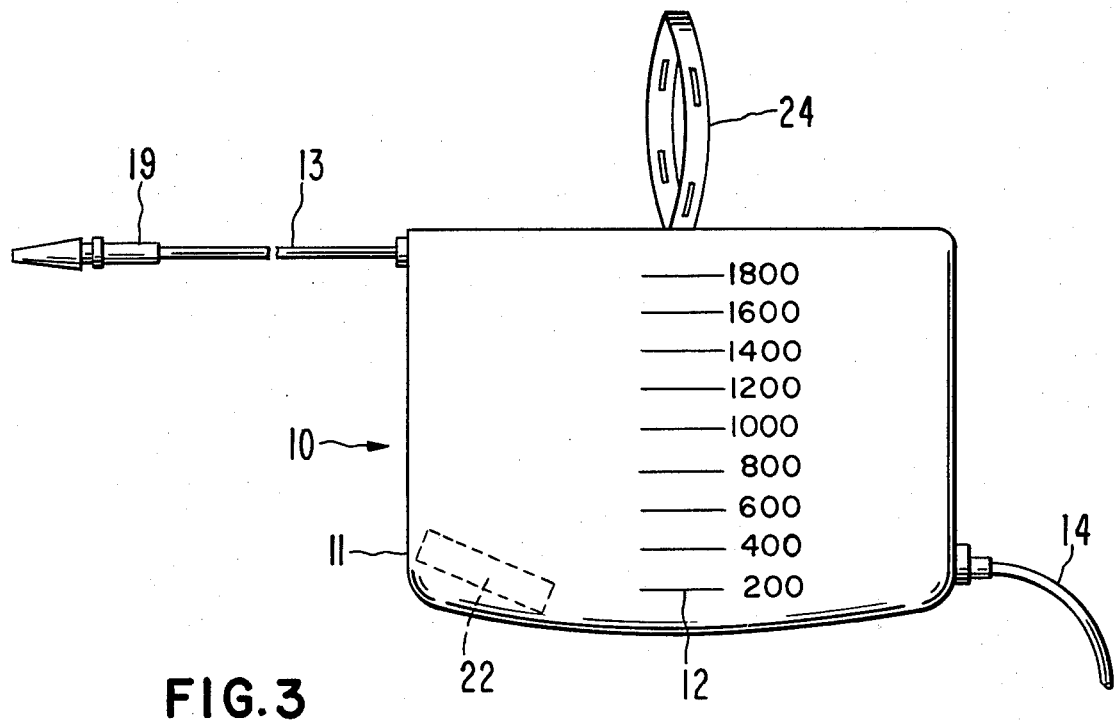

Turning now to the drawings in detail, which are examples of various embodiments of the invention, and which examples are not to be construed as limiting the invention, one embodiment of a novel patient care apparatus is indicated in FIG. 1 by the numeral 10. Apparatus 10 comprises a container 11 for receiving the storing a biological fluid, not shown, and has a volumetric scale 12 thereon for indicating the volume of fluid in container 11. Apparatus 10 has an inlet port, or inlet tube 13, for establishing fluid passage between the interior and the exterior of container 11. A flexible outlet port 14 for draining container 11 is positioned distant from port 13. Port 14 is equipped with a pinch clamp 15 for controlling the amount of fluid drained from container 11. Apparatus 10 acts in cooperation with a housing 16 equipped with end 17 adapted for communicating with inlet 13 and with end 18 adapted for receiving catheter 19. In the embodiment illustrated, device 16 has a male-end at 17 for inserting into a female-end of tube 13, and device 16 has a female-end at 18 for receiving a male-end of catheter 19. In another optional embodiment, device 16 has a female-end at 17, a male-end at 18, catheter 19 has a female-end and tube 13 has a male-end. Housing 16 provides an internal space 21 for holding a dispensing device, not shown in FIG. 1, and 16 is equipped with a one-way valve 20 for preventing fluid passage and pathogen migration from container 11 into ascending catheter 19.

FIG. 2 illustrates a patient care apparatus 10 embracing many of the features of apparatus 10 of FIG. 1. Apparatus 10 of FIG. 2 is structurally distinct from FIG. 1 by having a housing 16 intimately contacting and engaging container 11 through a retaining means, not shown, such as threads, a snap-on clamp, or the like. A dispensing device 22, is seen in housing 16 which device 22 is formed of a polymeric material containing a depolymerizable polymer. Device 22 has at least one surface 23 or a multiplicity of surfaces 23 for (a) releasing the depolymerizable polymer which is depolymerized in the presence of moisture in the apparatus to formaldehyde, and (b) imbibing moisture into the dispensing device for depolymerizing therein to formaldehyde which latter compound is released from the device. The formaldehyde substantially controls the multiplication of, and prevents migration of pathogens into ascending catheter 19.

FIG. 3 illustrates an embodiment of the invention comprising patient care apparatus 10, manufactured with the numbered features described above, and having dispensing device 22 within container 11 for controlling pathogens in apparatus 10. In this embodiment, apparatus 10 is made with a handle 24 for hanging the apparatus from a stand placed in the vicinity of a patient's bed.

ADDITIONAL DETAILS OF THE INVENTION

Dispensing device 22 used for the purpose of the invention consists of a body having a geometric shape that is sized and adapted for placement in a container 11 or in housing 16. Device 22 is formed with at least one surface for dispensing an agent from device 22 to the environment of use. The body of device 22 is made of a polymeric material and it contains the agent, the polymer paraformaldehyde selected from polymers of the general formula $(CH_2O)_n$ wherein n is 3 and of the general formula $HO(CH_2O)_{mH}$ wherein m is usually 3 to 125. The polymeric material permits passage of paraformaldehyde and formaldehyde from device 22. In operation when device 22 is in the environment of use, device 22 operates by releasing paraformaldehyde which is depolymerized by moisture in apparatus 10 to formaldehyde; or device 22 releases formaldehyde that is formed in device 22 by fluid entering and depolymerizing paraformaldehyde in device 22 to formaldehyde. In either operation the formaldehyde controls the multiplication of pathogens and prevents migration of pathogens into the ascending catheter and the patient. Exemplary pathogens that can cause urogenital infections which are subjected to the anti-pathogenic activity of formaldehyde include *Streptococcus faecalis, Proteus vulgaris, Staphylococcus aureus, Pseudomonas aeruginosa, Escherichia coli, Proteus mirabilis,* Klebsiella, Enterobacteriaceae and yeast, such as *Candida Albicans.*

Representative polymers suitable for forming device 22 include acrylic polymers and copolymers of methacrylate, ethyacrylate, ethylmethacrylate and methylmethacrylate; polymers and copolymers of vinyl chloride, N-vinylcarbazole, vinyl pyrrolidone and vinylidene chloride; polyvinyl-acetals such as polyvinyl formal, polyvinyl acetal and polyvinyl butyral; polyurethanes; polyolefins including polyethylene and polypropylene; polybutadiene, polyisoprene, silicone; ethylene-vinylacetate copolymers having a vinyl acetate content of 4 to 60%; and polyesters. The polymers can also optionally contain pigments and colorants for identifying the device. The amount of depolymerizable linear polymer expressed as paraformaldehyde in the polymeric material generally is about 0.001% to 60% by weight based on the total weight of the polymeric material forming device 22.

A dispensing device, 22, operable for the purpose of this invention was made as follows: first, 45 grams of powdered white solid paraformaldehyde were blended for 10 to 15 minutes at 35° to 40° C. on a two-roller mill with 55 grams of powdered, transparent ethylene-vinyl acetate copolymer, having a vinyl acetate content of 28% by weight, to produce a film consisting of a homogenous dispersion of paraformaldehyde in the copolymer. Next, the film was ground in a rotary knife grinder to produce particle sized 1/16 to ⅛ inches, averaged size, and the particles then transferred to the hopper of an extruder. Finally, the particles were extruded through a tubing die at 60° to 70° C. to yield the dispensing device. The device had an outside diameter of 5.2 mm, an inside diameter of 2.2 mm, and a length of 5 cm. The dispensing devices exhibited a steady-state delivery of formaldehyde, in the presence of moisture, of 220 µg/-hr-cm of device. The devices are stored in sealed aluminum foil packages to prevent premature production of formaldehyde.

The release rate of formaldehyde from the above devices were demonstrated in water solutions containing 0 to 5% sodium chloride corresponding to osmotic pressures of 0 to 43 atmospheres. The rate of formaldehyde release, expressed as the average steady-state release rate at listed sodium chloride concentration, is given in Table 1.

TABLE 1

| NaCl Concentration In Release Solutions (wt %) | Osmotic Pressure In Release Solutions (atm) | Steady-State Release Rate µg/hr-cm |
|---|---|---|
| 0 | 0 | 232 |
| 0.9 (Isotonic) | 7.9 | 220 |
| 2.4 | 20.3 | 226 |
| 5.0 | 43 | 196 |

In Table 1, wt% is the abbreviation for weight percent, atm for atmospheres, the steady-state release rate was measured for 30 to 240 hours and is expressed as µg/hr per cm of length of dispensing device. The data indicate five 5 cm dispensing devices of the above-described dimensions and parameters will deliver to a patient care apparatus 5 mg/hr for up to 10 days in a high osmolarity environment up to 43 atmospheres the needed formaldehyde. The data further indicate the release rate of formaldehyde is independent from the osmolarity of the release solution containing an osmagent such as the osmotic agent sodium chloride.

It will be understood by those versed in the medico-surgical and patient-care arts, that in the light of the present specification, drawings and the accompanying claims, this invention makes available to the art both a novel and useful combination patient care and dispensing device endowed with beneficial properties. And, while the invention can be used for collecting all kinds of biological fluids and other fluids, it will be further understood by those versed in the art that many embodiments of this invention can be made without departing from the scope of the invention. Accordingly, it is to be understood the invention is not to be construed as limited, but it embraces all equivalents inherent herein.

We claim:

1. A patient-care apparatus, comprising in combination: a container for receiving and storing a biological fluid; an inlet port in the container for establishing fluid passage between the interior and the exterior of the container; and a device in the container for substantially controlling the presence of pathogens in the apparatus, said device consisting of a body sized and adapted for prolonged placement in the container and having a surface exposed to the container, the body formed of a polymeric material containing paraformaldehyde, which is converted to formaldehyde when the apparatus is in use and released by the surface for controlling said pathogens.

2. The patient-care apparatus according to claim 1, wherein paraformaldehyde is a polymer selected from the group of polymers of the general formula consisting of $(CH_2O)_n$ wherein n is 3 and $HO(CH_2O)_m H$ wherein m is 3 to 125.

3. The patient-care apparatus according to claim 1, wherein the paraformaldehyde is converted to formaldehyde in the polymeric material in the presence of fluid that enters the material, and which formaldehyde is released by the device for substantially controlling the presence of pathogens in the container.

4. The patient-care apparatus according to claim 1, wherein the paraformaldehyde is dispensed by the device and converted to formaldehyde in the presence of moisture in the container for controlling the presence of pathogens in the container.

* * * * *